United States Patent
Hattori et al.

(10) Patent No.: US 12,295,301 B2
(45) Date of Patent: May 13, 2025

(54) PLANT CULTIVATION METHOD AND PLANT CULTIVATION APPARATUS

(71) Applicants: TOYOTA BOSHOKU KABUSHIKI KAISHA, Aichi (JP); Green Tech & Lab Co., Ltd., Tokyo (JP)

(72) Inventors: Yoko Hattori, Aichi (JP); Kazufumi Tabata, Aichi (JP); Hiroshi Suzuki, Kanagawa (JP)

(73) Assignees: TOYOTA BOSHOKU KABUSHIKI KAISHA, Aichi (JP); GREEN TECH & LAB CO., LTD., Tokyo (JP)

( * ) Notice: Subject to any disclaimer, the term of this patent is extended or adjusted under 35 U.S.C. 154(b) by 70 days.

(21) Appl. No.: 17/953,820

(22) Filed: Sep. 27, 2022

(65) Prior Publication Data
US 2023/0102988 A1   Mar. 30, 2023

(30) Foreign Application Priority Data
Sep. 29, 2021 (JP) .................. 2021-159013

(51) Int. Cl.
A01G 7/04 (2006.01)
(52) U.S. Cl.
CPC .................. A01G 7/045 (2013.01)
(58) Field of Classification Search
CPC ..................................... A01G 7/045
See application file for complete search history.

(56) References Cited

U.S. PATENT DOCUMENTS

| | | | | |
|---|---|---|---|---|
| 2014/0165462 A1* | 6/2014 | Shigyo | .................. | A01G 33/00 47/58.1 LS |
| 2014/0170733 A1 | 6/2014 | Shigyo et al. | | |
| 2017/0202154 A1 | 7/2017 | Yamamoto | | |
| 2018/0224093 A1* | 8/2018 | Dutta | ......................... | F21K 9/23 |
| 2020/0260651 A1 | 8/2020 | Ohtake et al. | | |

FOREIGN PATENT DOCUMENTS

| | | |
|---|---|---|
| CN | 103687478 | 3/2014 |
| CN | 103841818 | 6/2014 |
| CN | 110234222 | 9/2019 |
| JP | 2008-142005 | 6/2008 |

(Continued)

OTHER PUBLICATIONS

Office Action issued in Corresponding JP Patent Application No. 2021-159013, dated Oct. 3, 2024, along with an English translation thereof.

(Continued)

*Primary Examiner* — Magdalena Topolski
*Assistant Examiner* — Alanna K Peterson
(74) *Attorney, Agent, or Firm* — Greenblum & Bernstein, P.L.C.

(57) ABSTRACT

A plant cultivation method including irradiating a plant with first irradiation light including blue light and second irradiation light including red light. A first irradiation period T1 during which the first irradiation light is emitted and a second irradiation period T2 during which the second irradiation light is emitted are alternately provided in time series. The irradiation timings of the first irradiation light and the second irradiation light are determined by using a tide-generating force as an index.

6 Claims, 6 Drawing Sheets

(56) References Cited

FOREIGN PATENT DOCUMENTS

| | | |
|---|---|---|
| JP | 2009-125007 | 6/2009 |
| JP | 2012-179009 | 9/2012 |
| JP | 2015-204801 | 11/2015 |
| JP | 2016-54685 | 4/2016 |
| JP | 2017-85907 | 5/2017 |
| KR | 20180026954 A * | 9/2016 |

OTHER PUBLICATIONS

Office Action issued in Corresponding CN Patent Application No. 202211196761.X, dated Oct. 19, 2024, along with an English translation thereof.

* cited by examiner

PLANT CULTIVATION METHOD AND PLANT CULTIVATION APPARATUS

CROSS-REFERENCE TO RELATED APPLICATION

This application is based on and claims the priority of Japanese Patent Application No. 2021-159013 filed on Sep. 29, 2021, the entire contents of which are incorporated herein by reference.

BACKGROUND OF THE INVENTION

(1) Field of the Invention

The present disclosure relates to a plant cultivation method and a plant cultivation apparatus.

(2) Description of Related Art

In recent years, new plant cultivation methods have been contemplated, as disclosed in, for example, JP 2015-204801 A, JP 2016-54685 A, and JP 2017-85907 A.

SUMMARY OF THE INVENTION

However, the growth promoting effect of the conventional technique has not necessarily been sufficient and there has been a demand for a novel technique.

The present disclosure has been made in view of the above circumstances, and an objective thereof is to obtain a higher growth promoting effect. The present disclosure can be implemented in the following mode.

A plant cultivation method that irradiates a plant with first irradiation light including blue light and second irradiation light including red light, in which:
- a first irradiation period during which the first irradiation light is emitted and a second irradiation period during which the second irradiation light is emitted are alternately provided in time series; and
- irradiation timings of the first irradiation light and the second irradiation light are determined by using a tide-generating force as an index.

The plant cultivation method according to the present disclosure provides a high growth promoting effect on plants.

DETAILED DESCRIPTION OF PREFERRED EMBODIMENTS

Figure 1:
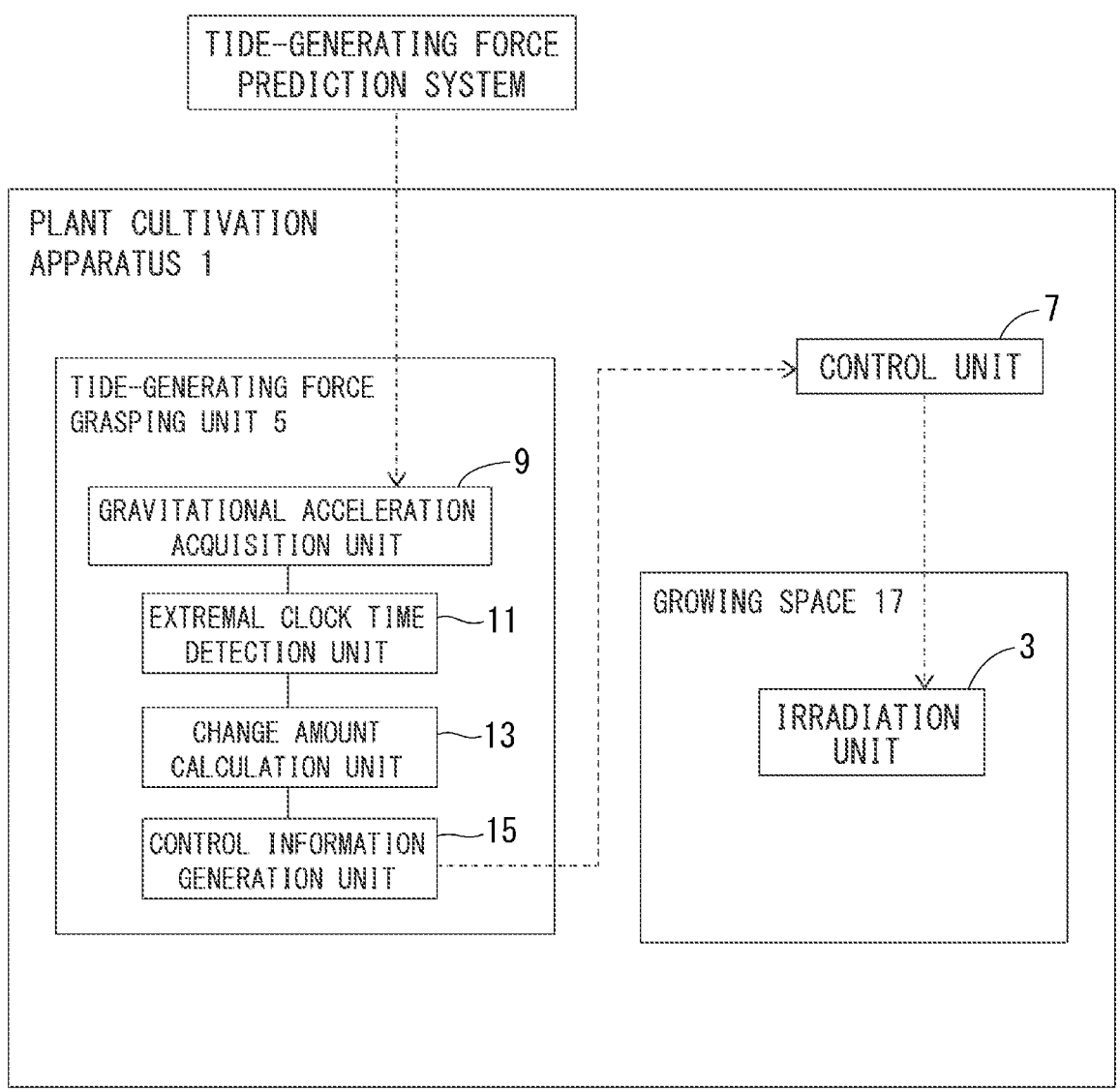
FIG. 1 is a block diagram illustrating a hardware configuration of an example of a plant cultivation apparatus.

Preferred examples of the present disclosure are described hereinafter.

A plant cultivation method that uses gravitational acceleration as an index of the tide-generating force, including:
during a predetermined period of time,
detecting, respectively as minimal clock times, all clock times at which a change of the gravitational acceleration becomes a minimal value, and detecting, respectively as maximal clock times, all clock times at which the change of the gravitational acceleration becomes a maximal value;
calculating, as a reduction amount, a value obtained by subtracting a value of the gravitational acceleration at each of the minimal clock times from a value of the gravitational acceleration at the maximal clock time immediately preceding each of the minimal clock times, for each of the minimal clock times; and
on the basis of a comparison result obtained by comparing the reduction amount at a specific minimal clock time selected from the minimal clock times with the reduction amounts at an immediately preceding minimal clock time immediately preceding the specific minimal clock time and at an immediately following minimal clock time immediately following the specific minimal clock time,
controlling the irradiation timing such that at least a part of a period between the specific minimal clock time and the maximal clock time immediately preceding the specific minimal clock time serves as the first irradiation period, in a case where the reduction amount at the specific minimal clock time is greater than the reduction amount at the immediately preceding minimal clock time and greater than the reduction amount at the immediately following minimal clock time.

A plant cultivation apparatus including:
an irradiation unit that irradiates a plant with first irradiation light including blue light and second irradiation light including red light;
a tide-generating force grasping unit that grasps a tide-generating force; and
a control unit that controls the irradiation unit, in which the control unit controls the irradiation unit to irradiate the plant with the first irradiation light and the second irradiation light on the basis of irradiation timings of the first irradiation light and the second irradiation light determined by using the tide-generating force as an index, such that a first irradiation period during which the plant is irradiated with the first irradiation light and a second irradiation period during which the plant is irradiated with the second irradiation light are alternately provided in time series.

The plant cultivation apparatus that uses gravitational acceleration as an index of the tide-generating force, including:
an extremal clock time detection unit that detects, during a predetermined period of time, respectively as minimal clock times, all clock times at which a change of the gravitational acceleration becomes a minimal value, and detects, respectively as maximal clock times, all clock times at which the change of the gravitational acceleration becomes a maximal value; and
a change amount calculation unit that calculates, as a reduction amount, a value obtained by subtracting a value of the gravitational acceleration at each of the minimal clock times from a value of the gravitational acceleration at the maximal clock time immediately preceding each of the minimal clock times, for each of the minimal clock times, in which the control unit controls the irradiation timing on a basis of a comparison result obtained by comparing the reduction amount at a specific minimal clock time selected from the minimal clock times with the reduction amounts at an immediately preceding minimal clock time immediately preceding the specific minimal clock time and at an immediately following minimal clock time immediately following the specific minimal clock time, such that at least a part of a period between the specific minimal clock time and the maximal clock time immediately preceding the specific minimal clock time serves as the first irradiation period, in a case where the reduction amount at the specific minimal clock time is greater than the reduction amount at the immediately preceding minimal clock time and greater than the reduction amount at the immediately following minimal clock time.

Hereinafter, the present disclosure is described in detail. In the present specification, the description of a numerical range using "to" is inclusive of the lower limit and the upper limit unless otherwise specified. For example, the expression "10 to 20" is inclusive of both the lower limit value "10" and the upper limit value "20". In other words, "10 to 20" has the same meaning as "no less than 10 and no more than 20".

1. Plant Cultivation Method

The plant cultivation method according to the present disclosure includes irradiating a plant with first irradiation light including blue light and second irradiation light including red light. A first irradiation period during which the first irradiation light is emitted and a second irradiation period during which the second irradiation light is emitted are alternately provided in time series. The irradiation timings of the first irradiation light and the second irradiation light are determined by using a tide-generating force as an index.

(1) First Irradiation Light

The first irradiation light includes blue light. Examples of the blue light include blue light having a central wavelength of 400 nm to 515 nm. Preferable blue light is blue light having a central wavelength of 400 nm to 460 nm. The first irradiation light is only required to include the blue light. The first irradiation light may include light having a wavelength different from that of the blue light. It is preferable that the first irradiation light does not include red light. It is more preferable that the first irradiation light consists of only the blue light. The wavelength of the blue light may be varied in the first irradiation period within the wavelength range presented above. The wavelength of the blue light may be varied between one irradiation cycle and another irradiation cycle. Typically, a proportion of the blue light to the total light quantity when the first irradiation light is emitted is at least 60%, more preferably at least 80%, and still more preferably 100%.

(2) Second Irradiation Light

The second irradiation light includes red light. Examples of the red light include red light having a central wavelength of 570 nm to 730 nm. Preferable red light is red light having a central wavelength of 645 nm to 680 nm. The second irradiation light is only required to include the red light. The second irradiation light may include light having a wavelength different from that of the red light. It is preferable that the second irradiation light does not include blue light. It is more preferable that the second irradiation light consists of only the red light. The wavelength of the red light may be varied in the second irradiation period within the wavelength range presented above. The wavelength of the red light may be varied between one irradiation cycle and another irradiation cycle. Typically, a proportion of the red light to the total light quantity when the second irradiation light is emitted is at least 60%, more preferably at least 80%, and still more preferably 100%.

(3) First Irradiation Period and Second Irradiation Period

During the first irradiation period, the first irradiation light is emitted. The period may be, for example, in hours (hr) as a unit of time, in days as a longer unit of time, or in minutes or seconds as shorter units of time.

During the second irradiation period, the second irradiation light is emitted. The period may be, for example, in hours (hr) as a unit of time, in days as a longer unit of time, or in minutes or seconds as a shorter unit of time.

The first irradiation period during which the first irradiation light is emitted and the second irradiation period during which the second irradiation light is emitted are alternately provided in time series. In other words, the first irradiation period and the second irradiation period are alternately provided along the time axis.

Specifically, for example, the first irradiation period and the second irradiation period may be provided in the following pattern. The patterns may be arbitrarily combined.

<Pattern 1>

The first irradiation period and the second irradiation period are alternately and consecutively provided.

<Pattern 2>

The first irradiation period and the second irradiation period are alternately provided with a pause period in which light irradiation is paused interposed therebetween. The pattern 2 includes a cycle in which the first irradiation period, the pause period, and the second irradiation period are provided in sequence in time series, and a cycle in which the second irradiation period, the pause period, and the first irradiation period are provided in sequence in time series.

<Pattern 3>

The first irradiation period and the second irradiation period are alternately provided while the first irradiation period and the second irradiation period are partially overlapped with each other. The pattern 3 includes a cycle in which the first irradiation period, an irradiation period in which the first irradiation light and the second irradiation light are emitted, and the second irradiation period are provided in sequence in time series, and a cycle in which the second irradiation period, an irradiation period in which the first irradiation light and the second irradiation light are emitted, and the first irradiation period are provided in sequence in time series.

When the first irradiation period and the subsequent second irradiation period are regarded as one irradiation cycle, the length of the first irradiation period in the one irradiation cycle is not particularly limited. The length of the first irradiation period is preferably no less than 2 hours and no longer than 13 hours, more preferably no less than 4 hours and no longer than 12 hours, and still more preferably no less than 6 hours and no longer than 10 hours, from the viewpoint of the growth promoting effect for plants.

The length of the second irradiation period in the one irradiation cycle is not particularly limited. The length of the second irradiation period is preferably no less than 12 hours and no longer than 22 hours, more preferably no less than 12 hours and no longer than 20 hours, and still more preferably no less than 12 hours and no longer than 18 hours, from the viewpoint of the growth promoting effect for plants.

The length of the one irradiation cycle may be varied between one irradiation cycle and another irradiation cycle. A ratio of the lengths of the first irradiation period and the second irradiation period in each irradiation cycle may be the same or different, and may be arbitrarily defined.

(4) Irradiation Timings

The irradiation timings of the first irradiation light and the second irradiation light are determined by using the tide-generating force as an index. For the tide-generating force, at least one of relative gravitational acceleration (theoretical value), a moon calendar, weather data (atmospheric pressure and tide level), and a distance from the center of the earth to the cultivation land may be used as the index. In the plant cultivation method of the present disclosure, it is preferable to use relative gravitational acceleration as an index of the tide-generating force. That is, it is preferable to grasp the relative gravitational acceleration and to control the irradiation timings of the first irradiation light and the second irradiation light according to the relative gravitational acceleration.

The relative gravitational acceleration (RGA) indicates a relative value of the gravitational acceleration with the standard gravitational acceleration (1 G=9.80665×108 μGal) as a reference (zero point).

The relative gravitational acceleration (hereinafter simply referred to as "gravitational acceleration") can be calculated by using a tidal force prediction program that is publicly available. Specifically, the relative gravitational acceleration at a target point and the temporal change thereof can be calculated by inputting information of the position (latitude and longitude) of a cultivation base, the date, and the time to the tidal force prediction program.

As the tidal force prediction program, for example, the tide prediction system "GOTIC2" (http://www.miz.nao.ac.jp/staffs/nao99/) or the like can be used.

Preferable irradiation timings are described in detail in the section "2. Plant cultivation apparatus 1" presented later.

(5) Light Quantities of First Irradiation Light and Second Irradiation Light The light quantities (intensities) of the first irradiation light and the second irradiation light are not particularly limited. For example, the respective photosynthetic photon flux densities (PPFD) are 1 to 1000 μmol/m² s, and preferably 10 to 500 μmol/m² s.

For example, the photosynthetic photon flux density of the first irradiation light is no less than 120 μmol/m² s, and the photosynthetic photon flux density of the second irradiation light is no less than 200 μmol/m² s. With such high photosynthetic photon flux densities of the second irradiation light and the first irradiation light, the growth effect for plants can be further enhanced.

In addition, the total accumulated light quantity of the irradiation light per day is not particularly limited. The accumulated light quantity is preferably no less than 7.2 mol/m², and more preferably no less than 10.8 mol/m².

The ratio of the light quantity (intensity) of the second irradiation light to that of the first irradiation light can be arbitrarily defined. It is preferable that "first irradiation light:second irradiation light" or "second irradiation light:first irradiation light" is in a range of about 1:1 to 20:1. It is particularly preferable that the ratio of light quantity "second irradiation light:first irradiation light" is 1:1 to 3:1. With this range, the growth of plants can be further promoted. In addition, the light quantities of the first irradiation light and the second irradiation light may be varied within the ranges presented above. For example, the light quantities may be varied within a certain irradiation cycle, or the light quantities may be varied between a certain irradiation cycle and another irradiation cycle.

(6) Carbon Dioxide Concentration

The carbon dioxide concentration in the first irradiation period and the second irradiation period is not particularly limited.

(7) Plant

In the present disclosure, the type of plant to be cultivated is not particularly limited.

Examples of the plant include angiosperms, gymnosperms, ferns, mosses, and fungi.

The angiosperm may be a dicotyledonous plant or a monocotyledonous plant. Among the angiosperms, plants from which fibers can be collected and vegetables (fruits vegetable, leaf vegetable, stalk vegetable, root vegetable, and flower vegetable) are preferable. Specific examples of the plant from which fibers can be collected include kenaf, hemp, jute, ramie, flax, Manila hemp, sisal hemp, gampi (*Diplomorpha sikokiana*), mitsumata (*Edgeworthia chrysantha*), kozo (*Broussonetia kazinoki*), banana, pineapple, curaua, coco palm, corn, sugar cane, bagasse, palm, papyrus, reed, esparto, sabai grass, wheat, rice plant, bamboo, cotton, and kapok. Furthermore, broad-leaved trees such as poplar, beech, birch, willow, and maple may also be exemplified. Among these, bast plants, that is, kenaf, hemp, jute, ramie, and flax are particularly preferable.

Specific examples of the vegetable include those belonging to: Malvales [Malvaceae (for example, okra, etc.), Tiliaceae (for example, mulukhiyah, etc.)]; Nymphaeales [Nymphaeaceae (for example, lotus, etc.)]; Violales [Cucurbitaceae (for example, cucumber, watermelon, melon, etc.)]; Apiales [Araliaceae (for example, udo, etc.), Apiaceae (for example, ashitaba (*Angelica keiskei*), celery, parsley, mitsuba (*Cryptotaenia japonica*), etc.)]; Caryophyllales [Chenopodiaceae (for example, spinach, etc.)]; Rosales [Rosaceae (for example, strawberry, etc.)]; Capparales [Brassicaceae (for example, turnip, cauliflower, bok choy, radish, Chinese cabbage, etc.)]; Fabales [Fabaceae (for example, adzuki bean, pea, soybean, peanut, etc.)]; Sapindales [Rutaceae (for example, Japanese pepper, etc.)]; Asterales [Asteraceae (for example, chrysanthemum, burdock, giant butterbur, lettuce, etc.)]; Scrophulariales [Pedaliaceae (for example, sesame, etc.)]; Lamiales [Lamiaceae (for example, perilla, basil, peppermint, etc.)]; Solanales [Solanaceae (for example, shishito pepper, potato, tomato, eggplant, bell pepper, etc.), Convolvulaceae (for example, sweet potato, etc.)]; Alismatales [Alismataceae (for example, arrowhead, etc.)]; Cyperales [Poaceae (for example, corn, etc.)]; Arales [Araceae (For example, konjac, taro, etc.)]; Zingiberales [Zingiberaceae (for example, ginger, myoga (*Zingiber mioga*), etc.)]; Liliales [Iridaceae (for example, saffron, etc.), Dioscoreaceae (for example, Chinese yam, etc.), Liliaceae (for example, asparagus, onion, garlic chive, etc.)]; and the like.

In addition, as the gymnosperm, those that can be collected as fibers are preferable. Specific examples thereof include softwood trees such as Japanese cedar, Japanese cypress, spruce, fir, pine, and larch.

Furthermore, the fern is preferably a vegetable. Specific examples thereof include those belonging to: Filicales [Polypodiaceae (for example, bracken, etc.), Osmundaceae (for example, Asian royal fern (*Osmunda japonica*), etc.)]; Equisetales [Equisetaceae (for example, horsetail, etc.)]; and the like.

In addition, the fungus is preferably a mushroom. Specific examples thereof include those belonging to: Auriculariales [Auriculariaceae (for example, jelly ear, etc.)]; Agaricales [Tricholomataceae (for example, enokitake (*Flammulina filiformis*), shiitake (*Lentinula edodes*), matsutake (*Tricholoma matsutake*), etc.), Agaricaceae (for example, common mushroom, etc.), Strophariaceae (for example, nameko (*Pholiota microspora*), etc.)]; and the like.

(8) Effects of Plant Cultivation Method of Present Disclosure

The plant cultivation method of the present disclosure determines the irradiation timings of the first irradiation light including the blue light and the second irradiation light including the red light by using the tide-generating force as an index when irradiating with a wavelength that is easily absorbed by plants, and thereby has an extremely high growth promoting effect on the plants.

When the first irradiation light including the blue light and the second irradiation light including the red light are emitted in a continuous and alternate manner, the timing of alternation is determined according to the tide-generating force (the lunar rhythm and the like), which has an extremely high growth promoting effect on the plants.

The plant cultivation method of the present disclosure has less energy loss than an irradiation method in which a general light source including a wide wavelength range is switched on and off.

Since the plant cultivation method of the present disclosure employs a relatively simple method of controlling light irradiation in a plant factory, existing equipment may be utilized in some cases, which reduces investment costs.

2. Plant Cultivation Apparatus 1

In the following description of a plant cultivation apparatus 1, the description of the various terms described in the above section "1. Plant cultivation method" is applicable as is. In the plant cultivation apparatus 1 described below, the irradiation timings of the first irradiation light including the blue light and the second irradiation light including the red light are described. The irradiation timings correspond to suitable irradiation timings in the above "1. Plant cultivation method".

The plant cultivation apparatus 1 includes an irradiation unit 3 which irradiates a plant with the first irradiation light including the blue light and the second irradiation light including the red light, a tide-generating force grasping unit 5 which grasps a tide-generating force, and a control unit 7 which controls the irradiation unit 3.

Figure 3:
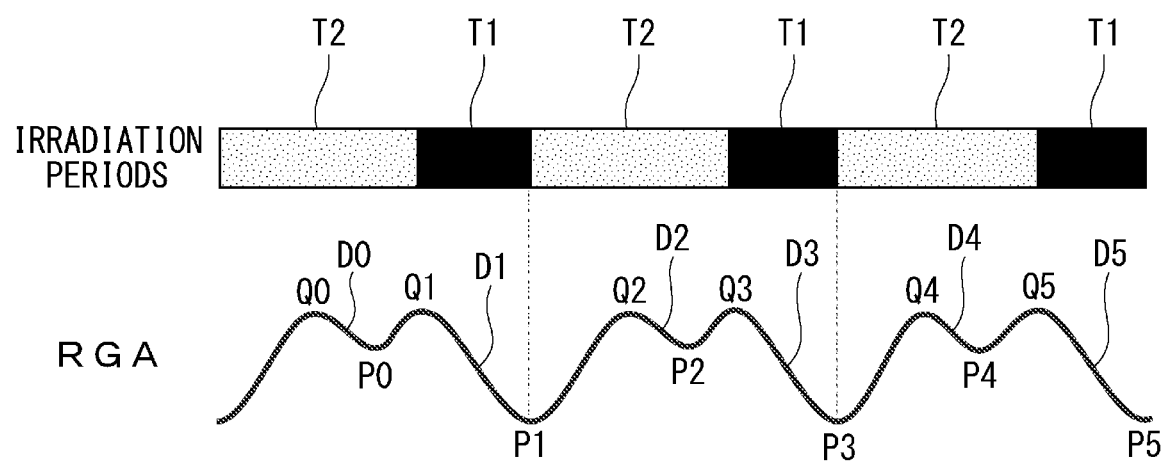
FIG. 3 is an explanatory diagram for explaining an example of a control pattern by a control unit of the plant cultivation apparatus.

The control unit 7 controls the irradiation unit 3 to irradiate the plant with the first irradiation light and the second irradiation light on the basis of the irradiation timings of the first irradiation light and the second irradiation light determined by using the tide-generating force as an index, such that a first irradiation period T1 during which the plant is irradiated with the first irradiation light and a second irradiation period T2 during which the plant is irradiated with the second irradiation light are alternately provided in time series (see FIG. 3).

The plant cultivation method of the present disclosure can be implemented by the plant cultivation apparatus 1.

The tide-generating force grasping unit 5 and the control unit 7 may be each realized by either of hardware and software. The tide-generating force grasping unit 5 and the control unit 7 may preferably be configured by providing a microcontroller (microcomputer) including a CPU, a memory (ROM, RAM, etc.), an input/output circuit, and the like along with a peripheral circuit such as an input/output interface. At least either one of the hardware and the software serves as the tide-generating force grasping unit 5 and the control unit 7. The control unit 7 and the tide-generating force grasping unit 5 may be separate or integrated.

The irradiation unit 3 is a lighting device that uses an LED, a light bulb, electroluminescence (EL), or the like as a light source. The control unit 7 can adjust the wavelength and light quantity (intensity) of the light emitted from the irradiation unit 3.

The plant cultivation apparatus 1 may include a plant growing space 17.

The tide-generating force grasping unit 5 uses a value of the gravitational acceleration as an index of the tide-generating force that affects the growth of the plant and the like. For this reason, there is provided a gravitational acceleration acquisition unit 9 that is connected to the known tide prediction system as described above or uses the tide prediction program, to receive an input of the value of the gravitational acceleration therefrom. The value of the gravitational acceleration thus acquired fluctuates with time, and is typically maximized and minimized repeatedly twice a day (see FIG. 2). In addition, the amplitude thereof (difference between the maximal value and the minimal value) also varies.

As illustrated in FIG. 1, the tide-generating force grasping unit 5 includes the gravitational acceleration acquisition unit 9, an extremal clock time detection unit 11, a change amount calculation unit 13, and a control information generation unit 15. The extremal clock time detection unit 11 and the change amount calculation unit 13 are configured to be able to use data of the gravitational acceleration in a predetermined period obtained by the gravitational acceleration acquisition unit 9. The predetermined period is a period in which the irradiation unit 3 is to be controlled, and the length of the period is not limited.

From the data of the gravitational acceleration in the predetermined period, the extremal clock time detection unit 11 detects, respectively as minimal clock times, all clock times at which a change of the gravitational acceleration becomes a minimal value, and detects, respectively as maximal clock times, all clock times at which the change of the gravitational acceleration becomes a maximal value.

The maximal clock times and the minimal clock times refer to clock times at which the gravitational acceleration, which fluctuates with time, has the maximal value and the minimal value respectively (hereinafter, the maximal clock time and the minimal clock time are also collectively referred to as extremal clock time). The clock time includes year, month, and day.

Figure 2:
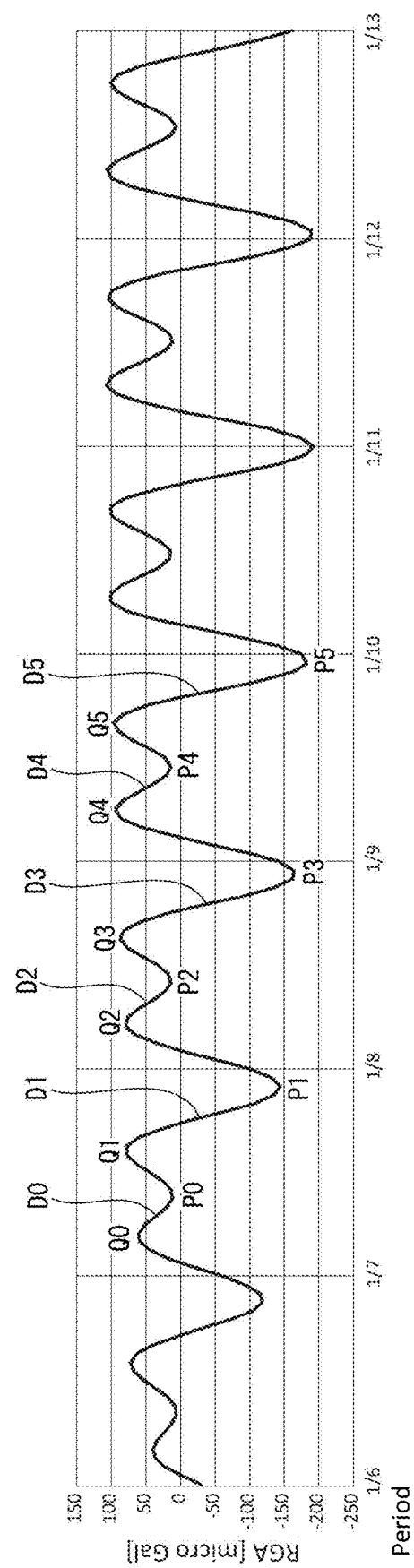
FIG. 2 is a graph showing an example of periodic fluctuation of the gravitational acceleration.

For example, in the graph shown in FIG. 2, all clock times at which a change of the gravitational acceleration becomes a minimal value P are detected respectively as minimal clock times, and all clock times at which the change of the gravitational acceleration becomes a maximal value Q are detected respectively as maximal clock times.

Note that FIG. 2 shows an example of periodic fluctuation of the gravitational acceleration. In the periodic fluctuation of the gravitational acceleration in FIG. 2, one cycle with a large fluctuation and one cycle with a small fluctuation are alternately observed. A day of the moon (about 24.8 hours) typically includes two cycles. As illustrated in FIG. 3, the control information generation unit 15 generates, as control information, information causing the first irradiation period T1 and the second irradiation period T2 to be alternately provided in time series.

The change amount calculation unit 13 calculates the magnitude of the peak of the gravitational acceleration at each extremal clock time within the predetermined period. The change amount calculation unit 13 calculates, for each minimal clock time, a value obtained by subtracting the value of the gravitational acceleration at each minimal clock time from the value of the gravitational acceleration at the maximal clock time immediately preceding each minimal clock time, as a reduction amount.

For example, a specific description is provided hereinafter with reference to the graph shown in FIG. 2.

<Regarding Minimal Value P0>

A value obtained by subtracting a value of the gravitational acceleration at a minimal clock time of a minimal value P0 from a value of the gravitational acceleration at a maximal clock time of a maximal value Q0 immediately preceding the minimal clock time of the minimal value P0 is calculated as a reduction amount D0.

<Regarding Minimal Value P1>

A value obtained by subtracting a value of the gravitational acceleration at a minimal clock time of a minimal value P1 from a value of the gravitational acceleration at a maximal clock time of a maximal value Q1 immediately preceding the minimal clock time of the minimal value P1 is calculated as a reduction amount D1.

<Regarding Minimal Value P2>

A value obtained by subtracting a value of the gravitational acceleration at a minimal clock time of a minimal value P2 from a value of the gravitational acceleration at a maximal clock time of a maximal value Q2 immediately preceding the minimal clock time of the minimal value P2 is calculated as a reduction amount D2.

<Regarding Minimal Value P3>

A value obtained by subtracting a value of the gravitational acceleration at a minimal clock time of a minimal value P3 from a value of the gravitational acceleration at a maximal clock time of a maximal value Q3 immediately preceding the minimal clock time of the minimal value P3 is calculated as a reduction amount D3.

<Regarding Minimal Value P4>

A value obtained by subtracting a value of the gravitational acceleration at a minimal clock time of a minimal value P4 from a value of the gravitational acceleration at a maximal clock time of a maximal value Q4 immediately preceding the minimal clock time of the minimal value P4 is calculated as a reduction amount D4.

<Regarding Minimal Value P5>

A value obtained by subtracting a value of the gravitational acceleration at a minimal clock time of a minimal value P5 from a value of the gravitational acceleration at a maximal clock time of a maximal value Q5 immediately preceding the minimal clock time of the minimal value P5 is calculated as a reduction amount D5.

The control information generation unit 15 generates control information for controlling the irradiation unit 3 on the basis of a comparison result obtained by comparing the reduction amount at a specific minimal clock time selected from the minimal clock times with the reduction amounts at an immediately preceding minimal clock time immediately preceding the specific minimal clock time and at an immediately following minimal clock time immediately following the specific minimal clock time.

For example, the comparison is made as follows.

<When Minimal Clock Time of Minimal Value P1 is Specific Minimal Clock Time>

The reduction amount D1 at the minimal clock time (specific minimal clock time) of the minimal value P1 is compared with the reduction amount D0 at the immediately preceding minimal clock time immediately preceding the specific minimal clock time (minimal clock time of the minimal value P0) and the reduction amount D2 at the immediately following minimal clock time immediately following the specific minimal clock time (minimal clock time of the minimal value P2).

<When Minimal Clock Time of Minimal Value P2 is Specific Minimal Clock Time>

The reduction amount D2 at the minimal clock time (specific minimal clock time) of the minimal value P2 is compared with the reduction amount D1 at the immediately preceding minimal clock time immediately preceding the specific minimal clock time (minimal clock time of the minimal value P1) and the reduction amount D3 at the immediately following minimal clock time immediately following the specific minimal clock time (minimal clock time of the minimal value P3).

<When Minimal Clock Time of Minimal Value P3 is Specific Minimal Clock Time>

The reduction amount D3 at the minimal clock time (specific minimal clock time) of the minimal value P3 is compared with the reduction amount D2 at the immediately preceding minimal clock time immediately preceding the specific minimal clock time (minimal clock time of the minimal value P2) and the reduction amount D4 at the immediately following minimal clock time immediately following the specific minimal clock time (minimal clock time of the minimal value P4).

<When Minimal Clock Time of Minimal Value P4 is Specific Minimal Clock Time>

The reduction amount D4 at the minimal clock time (specific minimal clock time) of the minimal value P4 is compared with the reduction amount D3 at the immediately preceding minimal clock time immediately preceding the specific minimal clock time (minimal clock time of the minimal value P3) and the reduction amount D5 at the immediately following minimal clock time immediately following the specific minimal clock time (minimal clock time of the minimal value P5).

As a result of the comparison, in a case where the reduction amount at the specific minimal clock time is greater than the reduction amount at the immediately preceding minimal clock time and greater than the reduction amount at the immediately following minimal clock time, the control information for controlling the irradiation timings is generated such that at least a part of a period between the specific minimal clock time and the maximal clock time immediately preceding the specific minimal clock time (hereinafter also referred to as "specific period") serves as the first irradiation period. Such control of the irradiation timings is only required to be performed in at least one of the specific periods. In other words, the control is not required to be performed in all the specific periods in the predetermined period.

The control information also includes the information causing the first irradiation period T1 and the second irradiation period T2 to be alternately provided in time series as described above.

For example, in the above example, in the case where the minimal clock time of the minimal value P1 serves as the specific minimal clock time, the reduction amount D1 of the specific minimal clock time is greater than the reduction amount D0 of the immediately preceding minimal clock time (D1>D0) and greater than the reduction amount D2 of the immediately following minimal clock time (D1>D2). In this case, the control information for controlling the irradiation timings is generated such that at least a part of a period between the specific minimal clock time (the minimal clock time of the minimal value P1) and the maximal clock time (the maximal clock time of the maximal value Q1) immediately preceding the specific minimal clock time serves as the first irradiation period T1 (see FIG. 3).

In addition, in the above example, in the case where the minimal clock time of the minimal value P3 serves as the specific minimal clock time, the reduction amount D3 of the specific minimal clock time is greater than the reduction amount D2 of the immediately preceding minimal clock time (D3>D2) and greater than the reduction amount D4 of the immediately following minimal clock time (D3>D4). In this case, the control information for controlling the irradiation timings is generated such that at least a part of a period between the specific minimal clock time (the minimal clock time of the minimal value P3) and the maximal clock time (the maximal clock time of the maximal value Q3) immediately preceding the specific minimal clock time serves as the first irradiation period T1 (see FIG. 3).

From the viewpoint of growth promotion of plants, the first irradiation period T1 is preferably no less than 50% and no greater than 100%, more preferably no less than 70% and no greater than 100%, still more preferably no less than 80% and no greater than 100% of the specific period.

It is preferable that a period other than the first irradiation period T1 serves as the second irradiation period T2.

In a day of the moon (about 24.8 hours), with the specific minimal clock time as a reference clock time, a clock time prior to the reference clock time by a predetermined time period may be set as the beginning of the first irradiation period T1, and the reference clock time may be set as the end of the first irradiation period T1. In this case, in a day of the moon (about 24.8 hours), a period other than the first irradiation period T1 may serve as the second irradiation period T2.

In the above example, in the case where the minimal clock time of the minimal value P2 serves as the specific minimal clock time, the reduction amount D2 of the specific minimal clock time is smaller than the reduction amount D1 of the immediately preceding minimal clock time (D2<D1) and smaller than the reduction amount D3 of the immediately following minimal clock time (D2<D3). In this case, the first irradiation period T1 is not provided in a period between the specific minimal clock time (the minimal clock time of the minimal value P2) and the maximal clock time (the maximal clock time of the maximal value Q2) immediately preceding the specific minimal clock time. In the case of FIG. 3, this period serves as the second irradiation period T2.

In a similar manner, for example, in the above example, in the case where the minimal clock time of the minimal value P4 serves as the specific minimal clock time, the reduction amount D4 of the specific minimal clock time is smaller than the reduction amount D3 of the immediately preceding minimal clock time (D4<D3) and smaller than the reduction amount D5 of the immediately following minimal clock time (D4<D5). In this case, the first irradiation period T1 is not provided in a period between the specific minimal clock time (the minimal clock time of the minimal value P4) and the maximal clock time (the maximal clock time of the maximal value Q4) immediately preceding the specific minimal clock time. In the case of FIG. 3, this period serves as the second irradiation period T2.

Figure 4:
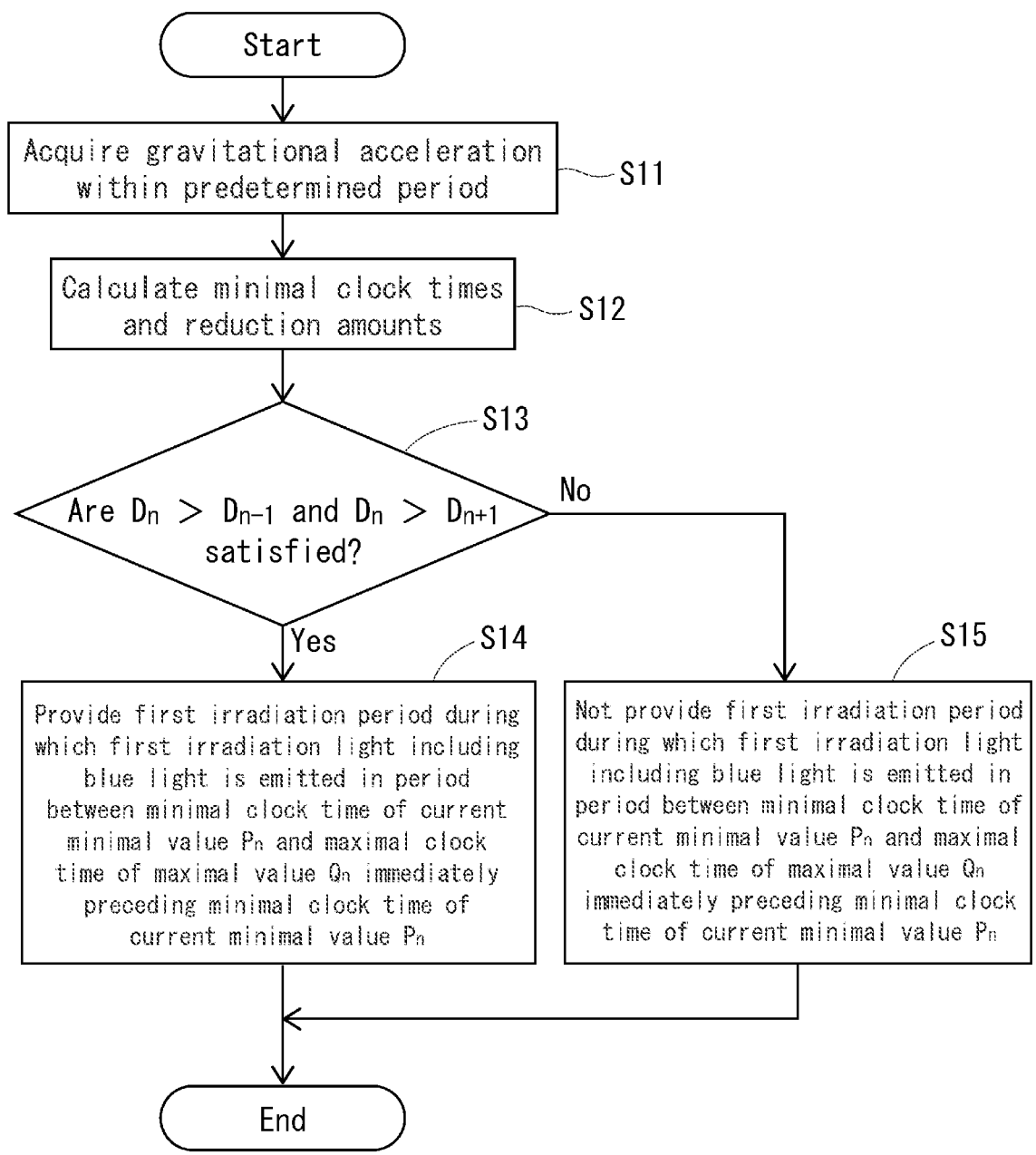
FIG. 4 is a flowchart for explaining an example of control by the control unit of the plant cultivation apparatus.

FIG. 4 is a flowchart showing an example of a process using gravitational acceleration as an index of the tide-generating force in the plant cultivation apparatus 1.

First, a point where plant cultivation is to be performed is specified by using the tide prediction program or the like, and a value of the gravitational acceleration in a desired period is acquired (step S11). The time interval at which the value of the gravitational acceleration is obtained is not particularly limited, and is only required to be such a time interval that the maximal value and the minimal value in the fluctuation can be detected. In the example shown in FIG. 2, a graph is drawn by using the value of the gravitational acceleration per hour. The value of the gravitational acceleration (gravitational acceleration data) at each clock time within the desired period acquired here can be stored so that it can be referred to in any of the following steps.

From the data of the gravitational acceleration, all clock times at which the change of the gravitational acceleration becomes the minimal value are detected as the minimal clock times respectively, and all clock times at which the change of the gravitational acceleration becomes the maximal value are detected as the maximal clock times respectively. In addition, for each minimal clock time, a value obtained by subtracting the value of the gravitational acceleration at the minimal clock time from the value of the gravitational acceleration at the maximal clock time immediately preceding the minimal clock time is calculated as the reduction amount (step S12).

Hereinafter, one minimal value of interest is referred to as a current minimal value $P_n$, a minimal value immediately preceding the current minimal value $P_n$ is referred to as $P_{n-1}$, and a minimal value immediately following the minimum value $P_n$ is referred to as $P_{n+1}$. For each minimal value $P_n$, the reduction amount of the gravitational acceleration from the immediately preceding maximal value $Q_n$ is referred to as $D_n$. Note that n is an integer of 2 or greater.

Then, for each minimal value, the reduction amount $D_n$ of the current minimal value $P_n$ is compared with the reduction amounts ($D_{n-1}$ and $D_{n+1}$) of the minimal values ($P_{n-1}$ and $P_{n+1}$) immediately preceding and following the current minimal value $P_n$, and the control information for controlling the irradiation unit 3 is generated on the basis of a result of the comparison.

Specifically, it is determined whether or not the reduction amount $D_n$ of the current minimal value $P_n$ is greater than the reduction amount $D_{n-1}$ of the immediately preceding minimal value $P_{n-1}$ ($D_n>D_{n-1}$) and greater than the reduction amount $D_{n+1}$ of the immediately following minimal value Pn+1 ($D_n>D_{n+1}$) (step S13).

In a case where the above conditions are satisfied (Yes in step S13), the control information is created such that at least a part of the period between the minimal clock time of the current minimal value $P_n$ and the maximal clock time of the maximal value $Q_n$ immediately preceding the minimal clock time is set as the first irradiation period T1 during which the first irradiation light including the blue light is emitted (step S14).

On the other hand, in a case where the above conditions are not satisfied (No in step S13), the first irradiation period T1 during which the first irradiation light including the blue light is emitted is not provided in the period between the minimal clock time of the current minimal value $P_n$ and the maximal clock time of the maximal value $Q_n$ immediately preceding the minimal clock time (step S15).

According to the above process, the first irradiation period T1 during which the first irradiation light including the blue light is emitted is sequentially provided, and the second irradiation period T2 during which the second irradiation light including the red light is emitted is provided between the first irradiation periods T1, and the control unit 7 thus controls the irradiation unit 3 such that the first irradiation period T1 and the second irradiation period T2 are alternately provided along a time axis (see FIG. 3).

The plant cultivation apparatus 1 of the present disclosure determines the irradiation timings of the first irradiation light including the blue light and the second irradiation light including the red light by using the tide-generating force as an index when irradiating with a wavelength that is easily absorbed by plants, and thereby has an extremely high growth promoting effect on the plants.

When the first irradiation light including the blue light and the second irradiation light including the red light are emitted in a continuous and alternate manner, the timing of alternation is determined according to the tide-generating force (the lunar rhythm and the like), which has an extremely high growth promoting effect on the plants.

The plant cultivation apparatus 1 of the present disclosure has less energy loss than an irradiation method in which a general light source including a wide wavelength range is switched on and off.

Since the plant cultivation apparatus 1 of the present disclosure employs a relatively simple method of controlling light irradiation in a plant factory, existing equipment may be utilized in some cases, which reduces investment costs.

EXAMPLES

Hereinafter, more specific descriptions are given by means of Examples.

1. Outline of Experiment

With respect to the plant cultivation method according to the present disclosure, the growth promoting effect was verified. As Example, there was adopted a method in which the irradiation timings of alternate irradiation of LEDs having different wavelengths were determined on the basis of the gravitational acceleration. As Comparative Example, a method was adopted in which the irradiation timings of alternate irradiation of LEDs having different wavelengths were determined on the basis of time.

(1) Experimental Method (1.1) Materials

Figure 5:
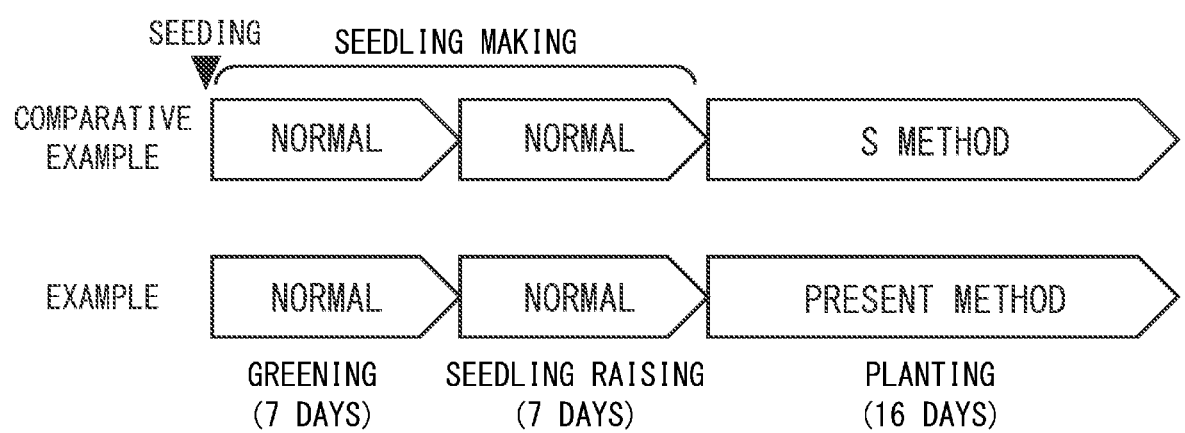
FIG. 5 is an explanatory diagram illustrating a plant cultivation method in an experiment.

In the experiment, leaf lettuce (cultivar: *Lactuca sativa* var. *crispa*) was used as an object of growth state observation. As shown in FIG. 5, growth was performed in the order of seedling making (greening and seedling raising) and planting.

(1.2) Cultivation Method

In both Example and Comparative Example, as the seedling making, the greening was performed for 7 days and the seedling raising was performed for 7 days on the basis of the conventional method.

Figure 6:
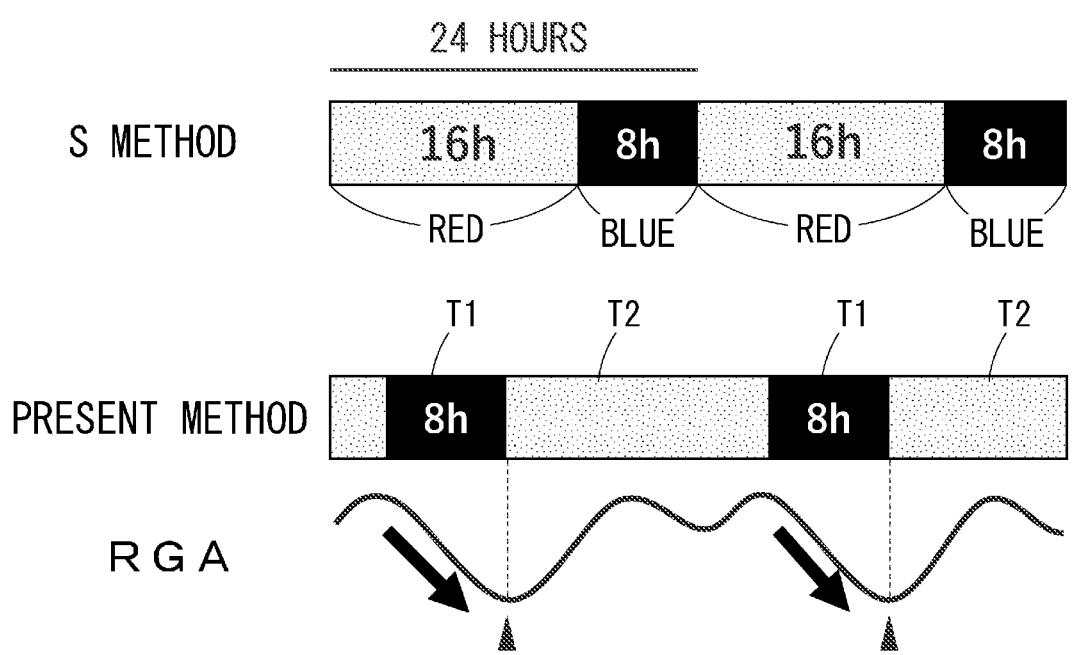
FIG. 6 is an explanatory diagram illustrating irradiation timings of first irradiation light and second irradiation light.

In Comparative Example, the S method (Shigyo method) was employed for planting. As shown in FIG. 6, in the S method, the lettuce was irradiated alternately with red light (660 nm) for 16 hours and with blue light (450 nm) for 8 hours. A period of the planting is 16 days.

In Example, the present method was employed for planting. The irradiation timings of the red light (660 nm) and the blue light (450 nm) were determined on the basis of the gravitational acceleration. Specifically, with the specific minimal clock time satisfying the aforementioned conditions $D_n > D_{n-1}$ and $D_n > D_{n+1}$ as the reference clock time, the clock time prior to the reference clock time by 8 hours was defined as the beginning of the first irradiation period T1 during which the blue light (450 nm) is emitted, and the reference clock time was defined as the end of the first irradiation period T1. A period other than the first irradiation period T1 was defined as the second irradiation period T2 of the red light (660 nm).

The total accumulated light quantity of the red light and the blue light per day was adjusted to be the same in Comparative Example and Example.

(1.3) Light Source

As a light source, a linear LED lamp having a similar shape to a fluorescent lamp was used. The light source includes the irradiation unit 3 having a red light emitting element composed of a red LED (central wavelength: 660 nm, wavelength range: 650 to 670 nm) and a blue light emitting element composed of a blue LED (central wavelength: 450 nm, wavelength range: 430 to 470 nm), and the control unit 7 which controls the irradiation unit 3 to turn on and off the red light emitting element and the blue light emitting element separately and independently.

(2) Results

An average 20% increase in fresh weight was observed in Example compared to Comparative Example. The experiment was carried out at n=36 in both Example and Comparative Example.

(3) Consideration

It was confirmed that the growth of the plant was promoted by determining the irradiation timings of the alternate irradiation of the blue light and the red light on the basis of the gravitational acceleration.

The foregoing examples are merely for illustrative purposes and are not to be construed as limiting the present disclosure. Although the present disclosure has been described with reference to typical embodiments, it is understood that the wording used in the description and the drawings of the present disclosure is not limiting, but illustrative and exemplary. As described in detail herein, modifications can be made within the scope of the appended claims, without departing from the scope or spirit of the present disclosure in its form. Although specific structures, materials, and Example have been referred to for detailed description of the present disclosure, it is not intended to limit the present disclosure to the recitations herein; rather, the present disclosure shall be deemed to encompass all functionally equivalent structures, methods, and uses within the scope of the appended claims.

The present disclosure is not limited to the embodiments described above in detail, and various modifications or changes can be made within the scope of the claims.

What is claimed is:

1. A plant cultivation method that irradiates a plant with a first irradiation light including a blue light and a second irradiation light including a red light and uses gravitational acceleration as an index of tide-generating force, comprising:

during a predetermined period of time, detecting, respectively as minimal clock times, all clock times at which a change of the gravitational acceleration becomes a minimal value, and detecting, respectively as maximal clock times, all clock times at which the change of the gravitational acceleration becomes a maximal value;

calculating, as a reduction amount, a value obtained by subtracting a value of the gravitational acceleration at each of the minimal clock times from a value of the gravitational acceleration at the maximal clock time immediately preceding each of the minimal clock times, for each of the minimal clock times; and on a basis of a comparison result obtained by comparing the reduction amount at a specific minimal clock time selected from the minimal clock times with the reduction amounts at an immediately preceding minimal clock time immediately preceding the specific minimal clock time and at an immediately following minimal clock time immediately following the specific minimal clock time, controlling the irradiation timing such that at least a part of a period between the specific minimal clock time and the maximal clock time immediately preceding the specific minimal clock time serves as a first irradiation period, in a case where the reduction amount at the specific minimal clock time is greater than the reduction amount at the immediately preceding minimal clock time and greater than the reduction amount at the immediately following minimal clock time, wherein the first irradiation period during which the first irradiation light is emitted and a second irradiation period during which the second irradiation light is emitted are alternately provided in time series; and irradiation timings of the first irradiation light and the second irradiation light are determined by using the tide-generating force as the index.

2. The plant cultivation method according to claim 1, wherein the first irradiation period is between 80% to 100% of the period of the specific minimal clock time and the maximal clock time immediately preceding the specific minimal clock time.

3. The plant cultivation method according to claim 1, wherein a period directly before and after the first irradiation period serves as the second irradiation period.

4. A plant cultivation apparatus comprising:

an irradiator that is configured to irradiate a plant with a first irradiation light including a blue light and a second irradiation light including a red light;

a tide-generating force identifier that is configured to identify a tide-generating force;

a controller that is configured to control the irradiator;

an extremal clock time detector that is configured to detect, during a predetermined period of time, respectively as minimal clock times, all clock times at which a change of the gravitational acceleration becomes a minimal value, and detects, respectively as maximal clock times, all clock times at which the change of the gravitational acceleration becomes a maximal value; and a change amount calculator that is configured to calculate, as a reduction amount, a value obtained by subtracting a value of the gravitational acceleration at each of the minimal clock times from a value of the gravitational acceleration at the maximal clock time immediately preceding each of the minimal clock times, for each of the minimal clock times, wherein the controller is configured to control the irradiator to irradiate the plant with the first irradiation light and the second irradiation light on a basis of irradiation timings of the first irradiation light and the second irradiation light determined by using the tide-generating force as an index, such that a first irradiation period during which the plant is irradiated with the first irradiation light and a second irradiation period during which the plant is irradiated with the second irradiation light are alternately provided in time series, and wherein the controller controls the irradiator on a basis of a comparison result obtained by comparing the reduction amount at a specific minimal clock time selected from the minimal clock times with the reduction amounts at an immediately preceding minimal clock time immediately preceding the specific minimal clock time and at an immediately following minimal clock time immediately following the specific minimal clock time, such that at least a part of a period between the specific minimal clock time and the maximal clock time immediately preceding the specific minimal clock time serves as the first irradiation period, in a case where the reduction amount at the specific minimal clock time is greater than the reduction amount at the immediately preceding minimal clock time and greater than the reduction amount at the immediately following minimal clock time.

5. The plant cultivation apparatus according to claim 4, wherein the first irradiation period is between 80% to 100% of the period of the specific minimal clock time and the maximal clock time immediately preceding the specific minimal clock time.

6. The plant cultivation method according to claim 4, wherein a period directly before and after the first irradiation period serves as the second irradiation period.

* * * * *